United States Patent [19]

Kohayakawa et al.

[11] Patent Number: 4,704,012

[45] Date of Patent: Nov. 3, 1987

[54] STEREOSCOPIC MICROSCOPE

[75] Inventors: Yoshimi Kohayakawa, Yokohama; Takashi Masuda, Kawasaki, both of Japan

[73] Assignee: Canon Kabushiki Kaisha, Tokyo, Japan

[21] Appl. No.: 788,785

[22] Filed: Oct. 18, 1985

[30] Foreign Application Priority Data

Oct. 23, 1984 [JP] Japan .............................. 59-222801
Mar. 29, 1985 [JP] Japan .............................. 60-67501

[51] Int. Cl.⁴ ............................................. G02B 21/22
[52] U.S. Cl. ...................................................... 350/516
[58] Field of Search .............................. 350/515–517, 350/131–132, 139, 522

[56] References Cited

U.S. PATENT DOCUMENTS 4,174,884 11/1979 Weissler ............................ 350/139
4,436,384 3/1984 Taira .................................. 350/515
4,601,550 7/1986 Yoshino et al. .................... 350/516

Primary Examiner—William H. Punter
Attorney, Agent, or Firm—Fitzpatrick, Cella, Harper & Scinto

[57] ABSTRACT

A stereoscopic microscope has an objective opposed to an object to be examined, having its optic axis in a horizontal plane and projecting a parallel light beam, a pair of imaging optical systems for right and left eyes disposed rearwardly of the objective, a pair of optical devices having an even number of reflecting surfaces inclining the optic axes of the imaging optical systems so as to provide a predetermined angle of depression and a predetermined convergence angle, an erector rotatable about the optic axes inclined by the optical devices for the adjustment of the eye width, and a pair of eyepieces for enlarging and observing the image of the object to be examined therethrough.

9 Claims, 9 Drawing Figures

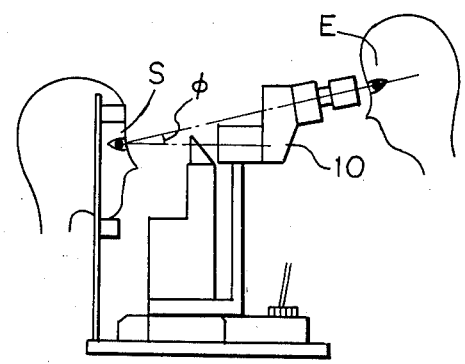
Fig. 6A
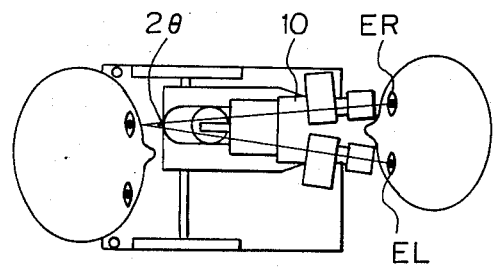
Fig. 6B
Fig. 7
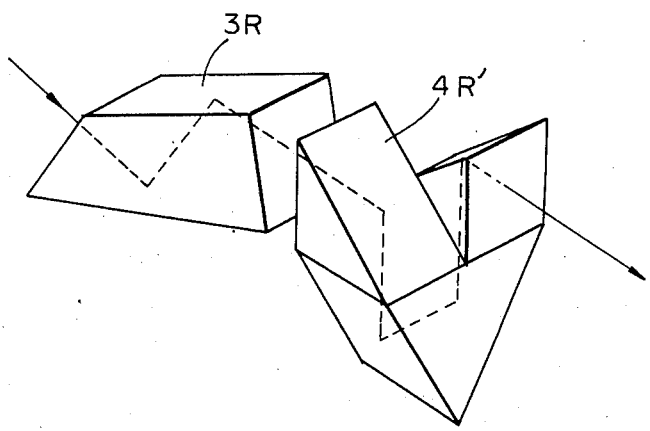

STEREOSCOPIC MICROSCOPE

BACKGROUND OF THE INVENTION

Field of the Invention

This invention relates to a stereoscopic microscope used, for example, for ophthalmic examination and having a Galilean type binocular stereoscopic microscope portion.

Description of the Prior Art

Heretofore, the Galilean type and the Greenough type optical systems have been widely used for the optical system of such a binocular stereoscopic microscope portion. In the Greenough type, entirely discrete two right and left microscopic optical systems are disposed so as to intersect each other at a predetermined angle, e.g. 10°–12° and therefore, the problem of convergence of eyes does not occur. In the Greenough type optical system, however, an objective, i.e. object glass is divided into two and therefore, for the purpose of magnification change, it is necessary to interchange the objective, and this leads to complexity and cumbersomeness. Also, the light beam is a convergent light and there is no portion in which the light beam becomes a parallel light beam and therefore, if an optical path dividing means is inserted to divide the optical path for a side view mirror or a camera from the intermediate portion of the lens barrel, the length of the optical path will be varied and thus, it is difficult to divide the optical path.

On the other hand, in the Galilean type, the optic axes entering the observer's eyes through eyepieces are parallel to each other and therefore, convergence must be effected as if an object actually perceived as lying nearby were at infinity. This leads to a disadvantage that it is difficult to stereoscopically view such an object. In the Galilean type optical system, however, the light beam emitted from a point on an object to be examined can be made into a parallel light beam by an objective and therefore, magnification change including that of the zoom optical system becomes simple. Also, there is a merit that various additional mechanisms can be mounted by inserting a beam splitter into the parallel light beam portion.

Japanese Utility Model Publication No. 19530 1983 and Japanese Laid-Open Patent Application No. 31992/1979 are known as the Galilean type optical systems improved so as to have a convergence angle.

The former has wedge prisms provided rearwardly of eyepieces, and the latter has prisms provided forwardly of eyepieces. Both of these have a disadvantage that the convergence angle changes when the adjustment of the eye width is effected. Furthermore, in the aforementioned Japanese Utility Model Publication No. 19530/1983, the wedge prisms provided rearwardly of eyepieces are close to the examiner's eyes, and this leads to a disadvantage that it is difficult for the examiner to see through the eyepieces.

Also, the natural line of vision of the human being has convergence and at the same time, looks somewhat downwardly when it sees a nearby object. Therefore, it is desired to provide an angle of depression to the observation optical axes to thereby reduce the fatigue of the examiner's eyes and facilitate the observation. However in these apparatuses, no consideration is given to the angle of depression.

Further, where a stereoscopic microscope of this type is used as a slit lamp or the like, in operation, the observer sees a region to be observed by the naked eye while keeping his eyes away from the stereoscopic microscope. Looking into the stereoscopic microscope is frequently repeated, but the observer need change his line of vision greatly when he sees the region to be observed while keeping his eyes away from the stereoscopic microscope. This is cumbersome to the observer.

SUMMARY OF THE INVENTION

It is an object of the present invention to make the best use of the merits of a Galilean type microscope optical system and eliminate the demerits thereof and to provide a stereoscopic microscope which enables the observer to obtain a suitable angle of depression, a suitable convergence angle and a suitable eye width.

It is also an object of the present invention to provide a stereoscopic microscope in which the angle of depression and the convergence angle are not varied by the adjustment of the eye width.

It is a further object of the present invention to provide a stereoscopic microscope which hardly requires the direction of the observer's line of vision to be changed during the observation through the stereoscopic microscope and during observation by the naked eye.

BRIEF DESCRIPTION OF THE DRAWINGS

FIG. 6A is a side view showing the positional relations among the region to be observed, the optical system and the observer for the determination of the angle of depression and the convergence angle.

FIG. 6B is a plan view corresponding to FIG. 6A.

FIG. 7 is a perspective view of an angle of depression and convergence angle prism and an erecting optical system or prism.

DESCRIPTION OF THE PREFERRED EMBODIMENTS

Figure 1:
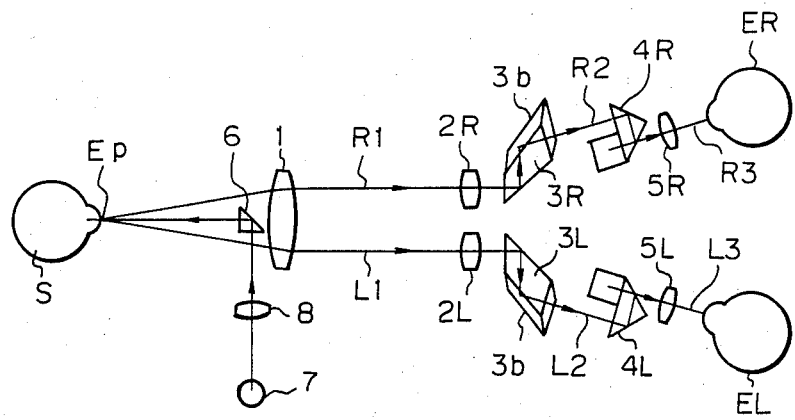
FIG. 1 is a plan view of an entire optical arrangement.

The invention will hereinafter be described in detail with respect to some embodiments thereof shown in the drawings.

FIG. 1 is a plan view showing an embodiment in which the present invention is applied to an ophthalmic stereoscopic microscope, and more particularly showing only a binocular stereoscopic microscope portion. In FIG. 1, letter S designates an eye to be examined, and reference characters R1, R2, R3 and L1, L2, L3 denote optic axes corresponding to the observer's right eye ER and left eye EL, respectively. Behind a common objective 1 having its optic axis lying in a horizontal plane and projecting a parallel light beam, relay lenses 2R, 2L, overlooking prisms 3R, 3L having an even number of reflecting surfaces deflecting the optical paths, erecting optical system or prisms 4R, 4L constituting an erector and eyepieces 5R, 5L are successively arranged on the optical axes R1, R2, R3 and L1, L2, L3, respectively. Forwardly of the objective 1, there is disposed a light dividing member 6 comprising a prism of an illuminating optical system. This illuminating optical system is comprised of an illuminating light source 7, an illuminating lens 8 and the aforementioned light dividing member 6 arranged in succession.

A light beam emitted from the illuminating light source 7 is imaged at the imaging position Ep of the eye S to be examined by the illuminating lens 8 through the light dividing member 6. The imaging position Ep is made coincident with the object measuring focus position of the objective 1, and the light beam from the imaging position Ep is made into a parallel light beam by the objective 1 and passes through the relay lenses 2R, 2L into the overlooking prisms 3R, 3L.

Figure 2:
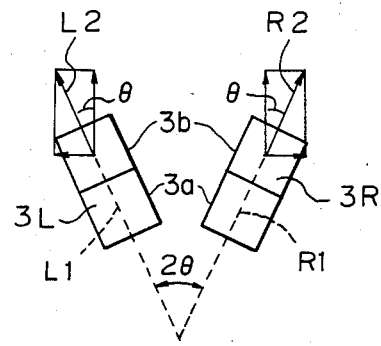
FIG. 2 is a front view of overlooking prisms as seen from the direction of the optic axis.
Figure 3A:
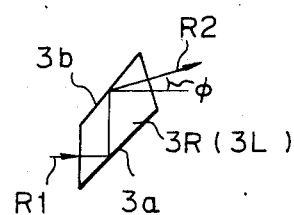
FIGS. 3A and 3B are side views of the overlooking prism and mirrors, respectively.

Each of the overlooking prisms 3R, 3L is a prism having two reflecting surfaces not parallel to each other as shown in the persspective view of FIG. 7. FIG. 2 shows the overlooking prisms 3R, 3L as seen from the directions of the optic axes R1, L1. The overlooking prisms 3R, 3L are installed while being inclined by an angle $\theta$ with respect to the vertical direction and therefore, the light beams having entered the overlooking prisms 3R, 3L are each reflected in a direction inclined by an angle $\theta$ with respect to the vertical direction by a first reflecting surface 3a as indicated by a broken line and enter a second reflecting surface 3b. On the second reflecting surface 3b, the light beams emerge in the same direction when viewed from the optic axes R1, L1, but when viewed from the side as shown in the side view of FIG. 3A, the light beams emerge while being inclined by an angle $\phi$ with respect to the horizontal plane because the first reflecting surface 3a and the second reflecting surface 3b are not parallel to each other. Thus, the optic axes R2, L2 are inclined by $\phi$ with respect to the optic axes R1, L1.

Figure 4:
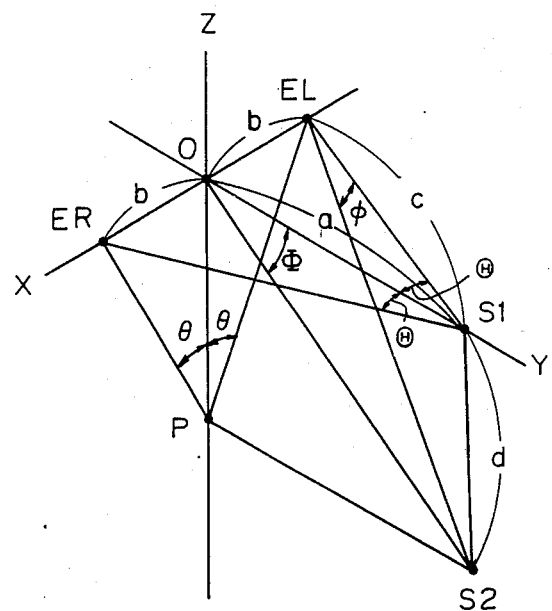
FIG. 4 illustrates the relations among the angle of depression, the convergence angle, $\theta$ and $\phi$.

Here, the suitable values of the angles $\theta$ and $\phi$ will be considered. Generally, the angle of depression in the direction of the natural line of vision of the human being is approximately 15°, and the convergence angle is approximately 7° for both of the left and right eyes when it is assumed that they see 250 mm ahead. Assuming that the angle of depression is $\Phi$ and the convergence angle is $\widehat{H}$, the relations among $\Phi$, $\widehat{H}$, $\phi$ and $\theta$ may be represented by an XYZ orthogonal coordinate system shown in FIG. 4. If the centers of the right and left observing eyes ER and EL disposed on the X-axis are the origin O and it is assumed that the observing eyes ER and EL see the direction of the Y-axis and the position of the object when the convergence angle is $\widehat{H}$ and the angle of depression is 0° is S1 on the Y-axis and the position of the object when the convergence angle is $\widehat{H}$ and the angle of depression is $\Phi$ is S2 on a plane YZ and the point at which S2 is projected onto the Z-axis and the angle ELPER = $2\theta$ is P and the distance S1O=a and OEL=b and S1EL=c and OP=S1S2=d, then $$\tan \widehat{H} = b/a \qquad (1)$$

$$\tan \Phi = d/a \qquad (2)$$

$$\cos \widehat{H} = a/c \qquad (3)$$

$$\tan \theta = b/d \qquad (4)$$

$$\tan \phi = d/c \qquad (5)$$

Accordingly, from equations (1), (2) and (4), $$\tan \theta = b/d = (b/a)/(d/a) = \tan \widehat{H}/\tan \Phi \qquad (6).$$

Also, from equations (2), (3) and (5), $$\tan \phi = d/c = (a/c) \cdot (d/a) = \cos \widehat{H} \cdot \tan \Phi \qquad (7).$$

If said 7° and 15° are substituted into the convergence angle $\widehat{H}$ and the angle of depression $\Phi$, respectively, of equations (6) and (7), the angles $\theta$ and $\phi$ can be found, that is, $\theta = 24.6°$ and $\phi = 14.9°$.

Accordingly, if the overlooking prisms 3R, 3L having the reflecting surface 3b inclined so that $\phi = 14.9°$ are obliquely disposed so that $\theta = 24.6°$, there can be obtained a stereoscopic microscope through which observation can be effected most easily.

Figure 3B:
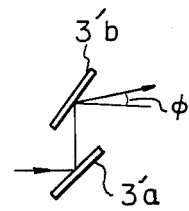

As shown in FIG. 3B, the overlooking prisms 3R and 3L may be replaced by mirrors 3'a and 3'b having similar reflecting surfaces. Also, the reflecting surfaces may be an even number of surfaces instead of two surfaces and in that case, image rotation will not occur even if reflection takes place an even number of times and therefore, various prisms or mirrors having an even number of reflecting surfaces can be used if they are prisms or mirrors in which finally the angle of depression and the convergence angle can be of suitable values.

The light beams having emerged from the overlooking prisms 3R and 3L enter erecting optical systems or prisms 4R and 4L. Generally, each of the erecting optical systems or prisms 4R and 4L are comprised of two rectangular prisms combined together and has the function of converting an inverted image into an erect image. In this embodiment, so-called porro prisms are used as the erecting optical systems or prisms 4R and 4L and are installed for rotation about the optic axes R2 and L2, respectively, in order to adjust the eye width. From the nature of the porro prisms, even if the optical systems 4R and 4L are rotated about the optic axes R2 and L2, respectively, the angles of the observation optic axes R3 and L3 are maintained invariable even during the adjustment of the eye width and the angle of depression and the convergence angle do not vary because the observation optic axes R3 and L3 are always parallel to the optic axes R2 and L2, respectively. Also, from the structure of the porro prisms, the distance to the eye S to be examined can be shortened. Although the porro prisms have been used here, it is also possible to use so-called eye width adjusting prisms such as diamond-shaped prisms.

The light beams having emerged from the optical systems 4R and 4L enter the observer's eyes ER and EL, respectively, through eyepieces 5R and 5L constituting eyepieces for enlarging and observing the object image therethrough, whereby the observer can stereoscopically observe the eye S to be examined.

Figure 5:
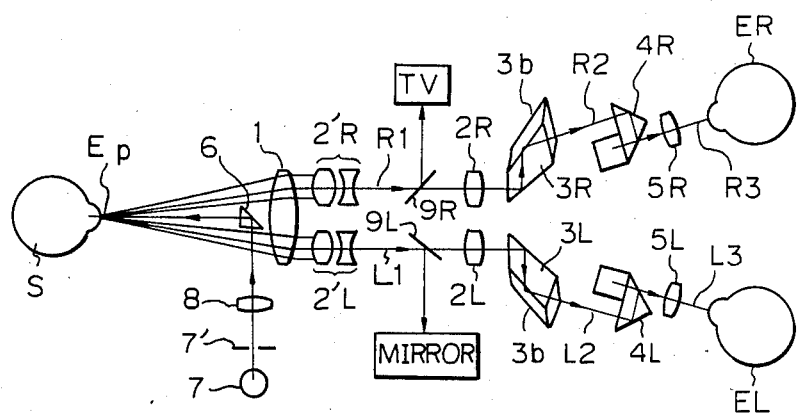
FIG. 5 shows a modification in which a zoom lens and optical path dividing means are added.

The optic axes R1 and L1 from the objective 1 to the overlooking prisms 3R and 3L are parallel to each other as shown in FIG. 5 and therefore, magnification changing optical systems 2'R, 2'L and beam splitters 9R, 9L for dividing the light to a photographing apparatus or a side view mirror can be inserted onto the optic axes R1 and L1, thereby making the best use of the merits of the Galilean type. Although, in the present embodiment, no slit is inserted into the illuminating optical system, use may be made of a slit illuminating optical system having a slit 7' as shown in FIG. 5. Further, although the present embodiment has been described with respect to an ophthalmic stereoscopic microscope, this stereoscopic microscope can of course be widely applied not only to the ophthalmic field, but also to various fields such as medical treatments, researches and industries.

FIGS. 6A and 6B show an embodiment in which means for forming the angle of depression and the convergence angle adjusts the angle of depression and the convergence angle to the imaging point of an objective. Assuming that, as shown in the side view of FIG. 6A, the angle of depression at which the observer actually sees the region to be observed of the eye S to be examined, i.e., the imaging point of the objective, without the intermediary of a stereoscopic microscope 10 is $\phi$, the angle of inclination $\phi$ of overlooking prisms 3R, 3L is also adjusted to the same magnitude. Also, assuming that, as shown in the plan view of FIG. 6B, the convergence angle at which the observer's eyes ER and EL actually see the region to be observed without the intermediary of the stereoscopic microscope 10 is $2\theta$, the overlooking prisms 3R, 3L are disposed while being inclined at the same angle $\theta$ with respect to the optic axis. When the angles $\phi$ and $\theta$ are determined in this manner, the observer can stereoscopically observe the region to be observed as easily through the stereoscopic microscope 10 as when he actually observes said region and, even when he sees the region to be observed by his naked eyes while keeping his eyes away from the stereoscopic microscope 10, he need not change the angle of depression and the convergence angle. Adjustment of the angle of depression and the convergence angle to the imaging point of the objective lens can also be appled to a Greenough type stereoscopic microscope.

Also, the formation of the angle of depression and the convergence angle can be accomplished not only by reflection, but also by refraction by the use of a wedge type prism, for example. In the case of the formation by reflection, there is no chromatic aberration and therefore, during the observation, there is no problem resulting from chromatic aberration such as color blur.

What we claim is:

1. A stereoscopic microscope provided with:

an objective opposed to an object to be examined, having its optic axis in a horizontal plane and projecting a parallel light beam;

a pair of imaging optical systems for right and left eyes disposed rearwardly of said objective;

a pair of optical means having an even number of reflecting surfaces inclining the optic axes of said imaging optical systems so as to provide a predetermined angle of depression and a predetermined convergence angle;

an erector rotatable about the optic axes inclined by said optical means for the adjustment of the eye width; and a pair of eyepieces for enlarging and observing the image of said object to be examined therethrough.

2. A stereoscopic microscope according to claim 1, wherein said optical means are prisms.

3. A stereoscopic microscope according to claim 1, wherein said optical means are an even number of mirrors.

4. A stereoscopic microscope according to claim 1, wherein said erector is an erecting optical system.

5. A stereoscopic microscope according to claim 4, wherein said erect prism is a porro prism comprising rectangular prisms combined together.

6. A stereoscopic microscope according to claim 1, further provided with an illuminating optical system for illuminating the object to be examined.

7. A stereoscopic microscope according to claim 6, wherein the illuminated area of the object to be examined is slit-like.

8. A stereoscopic microscope according to claim 6, wherein said illuminating optical system is provided with a light dividing member near said objective.

9. A stereoscopic microscope according to claim 1, wherein said optical means adjust the angle of depression and the convergence angle to the imaging point of said objective.

* * * * *